United States Patent
Liu et al.

(10) Patent No.: US 9,072,762 B2
(45) Date of Patent: Jul. 7, 2015

(54) NATURAL COMPOSITION TO DECREASE EFFECTS OF A HIGH FAT DIET

(71) Applicants: Zhijun Liu, Baton Rouge, LA (US); Peiying Yang, Sugarland, TX (US)

(72) Inventors: Zhijun Liu, Baton Rouge, LA (US); Peiying Yang, Sugarland, TX (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/746,630

(22) Filed: Jan. 22, 2013

(65) Prior Publication Data

US 2014/0206634 A1    Jul. 24, 2014

Related U.S. Application Data

(62) Division of application No. 12/761,798, filed on Apr. 16, 2010, now abandoned.

(60) Provisional application No. 61/170,341, filed on Apr. 17, 2009.

(51) Int. Cl.
| | |
|---|---|
| *A61K 31/704* | (2006.01) |
| *A61K 31/192* | (2006.01) |
| *A61K 31/366* | (2006.01) |

(52) U.S. Cl.
CPC ............ *A61K 31/704* (2013.01); *A61K 31/192* (2013.01); *A61K 31/366* (2013.01)

(58) Field of Classification Search
CPC . A61K 31/192; A61K 31/366; A61K 31/704; A61K 45/06
See application file for complete search history.

(56) References Cited

U.S. PATENT DOCUMENTS

2007/0054868 A1   3/2007  Weinstein ..................... 514/27

FOREIGN PATENT DOCUMENTS

JP         2001-48727      2/2001

OTHER PUBLICATIONS

Bråkenhielm, E., Cao, R., Gao, B., Angelin, B., Cannon, B., Parini, P., & Cao, Y. (2004). Angiogenesis inhibitor, TNP-470, prevents diet-induced and genetic obesity in mice. Circulation research, 94(12), 1579-1588.*

Snodgrass, W. R. (2001). Herbal products: risks and benefits of use in children. Current therapeutic research, 62(10), 724-737.*
Bicknell, R., "Vascular targeting and the inhibition of angiogenesis," Annals of Oncology, vol. 5, pp. 45-50 (1994).
Chou, G. et al., "Quantitative and fingerprint analyses of Chinese sweet tea plant (*Rubus suavissimus* S. Lee)," J. Agric. And Food Chem., vol. 57, pp. 1076-1083 (2009).
Creamer, D. et al., "Overexpression of the angiogenic factor platelet-derived endothelial cell growth factor/thymidine phosphorylase in psoriatic epidermis,"Br. J. Dermatol., vol. 137, pp. 851-855 (1997).
Eerola, A.K. et al., "Tumour infiltrating lymphocytes in relation to tumour angiogenesis, apoptosis," Lung Cancer, vol. 26, pp. 73-83 (1999).
Gao et al., "19α-Hydroxyursane-Type Triterpene ?Glucosyl Esters from the Roots of *Rubus suavissimus* S.Lee," Che. Pharm. Bull., vol. 33, pp. 37-40 (1985).
Gasparini, G., "The rationale and future potential of angiogenesis inhibitors in neoplasia," Drugs, vol. 58, pp. 17-38 (1999).
Hirono, S. et al., "Sweet and bitter diterpene-glucosides from leaves of *Rubus suavissimus*," Chem. Pharm. Bull., vol. 38, pp. 1743-1744 (1990).
Hunag, P. et al., "Complex utilization of *Rubus suavissimus* S. Lee," Guangxi Chem. Industry, vol. 31, pp. 24-25 (2002).
Kotaro, U., "Antiallergy action of *Rubus suavissimus*," Shokuhin Kogyo, vol. 40, pp. 52-59 (1997) (with translation).
Li, H. et al., "Rubusiviis A-F, monomeric and oligomeric ellagitan-nins from Chinese sweet tea and their ?-amylase inhibitory activity," Chem. Pharm. Bull., vol. 55, pp. 1325-1331 (2007).
Liu, D. et al., "Bioassay-guided fractionation of *Rubus suavissimus* leaf extracts possessing NF-?B inhibitory activities and a separable cytoxicity," Pharm. Biol., vol. 43, pp. 713-717 (2005).
Liu, Z. et al., "Gallic acid is partially responsible for the antiangiogenic activities of *Rubus* leaf extract," Phytother. Res., vol. 20, pp. 800-813 (2006).
Maniotis, A.J. et al., "Vascular channel formation by human melanoma cells in vivo and in vitro: Vasculogenic mimicry," Am. J. Pathol., vol. 155, pp. 739-752 (1999).

(Continued)

*Primary Examiner* — Shaojia Anna Jiang
*Assistant Examiner* — Dale R Miller
(74) *Attorney, Agent, or Firm* — John H. Runnels; Bonnie J. Davis

(57) ABSTRACT

The combination of gallic acid, ellagic acid, and rubusoside was shown to inhibit angiogenesis by inhibition of pro-angiogenic factors. These three compounds were shown to be absorbed from the intestine making the compounds orally bioavailable. The ratio of the three compounds in the composition was a weight ratio of approximately 1:1.7:17.0 of gallic acid, ellagic acid, and rubusoside, respectively, resulting in a composition with 5% w/w gallic acid, 9% w/w ellagic acid, and 86% w/w rubusoside. This combination was also shown to reduce weight gain, fat accumulation, and serum cholesterol in mammals fed a high fat diet. It also reduced serum triglycerides and tended to reduce blood glucose in mammals on both normal and high fat diets. This three-compound composition ("GER") can be used to treat diseases associated with angiogenesis and to decrease effects of a high fat diet.

7 Claims, 12 Drawing Sheets

(56) References Cited

OTHER PUBLICATIONS

Nakahara, K., "Anti-allergic activity of Tiencha and oolong tea polyphenols," Food Style 21, vol. 2, pp. 45-49 (1998) (with translation).
Ohtani, . et al., "Minor diterpene glycosides from sweet leaves of *Rubus suavissimus*," Phytochemistry, vol. 31, pp. 1553-1559 (1992).
Ono, Y., "The health beneficial effects of Tien-cha (*Rubus suavissimus* tea) and its applications," Food Style 21, vol. 6, pp. 77-80 (2002) (with translation).
Rosen, L., Antiangiogenic strageties and agents in clinical trials, Oncologist, vol. 5, Supp. 1, pp. 20-27 (2000).
Rupnick, M.A. et al., "Adipose tissue mass can be regulated through the vasculature," PNAS, vol. 99, pp. 10730-10735 (2002).
Seto, T. et al., "β-Glucosyl esters of 19α-hydroxyursolic acid derivatives in leaves of *Rubus* species," Phytochemistry, vol. 23, Issue 12, pp. 2829-2834 (1984).
Tanaka, T. et al., "Rubusoside (β-D-glucosyl ester of 13-O-β-D-glucosyl-steviol), a sweet principle of *Rubus chingii* Hu (Rosacease)," Agricultural and Biological Chemistry, vol. 45, No. 9, pp. 2165-66 (1981).
Thielecke, F. et al., "The potential role of green tea catechins in the prevention of metabolic syndrome—a review," Phytochem., vol. 70, pp. 11-24 (2009).
Wenger, F.A. et al., "Tumor size and lymph-node status in pancreatic carcinoma—is there a correlation to the preoperative immune function?," Langenbecks Archives of Surgery, vol. 384, pp. 473-478 (1999).
Wolfram, S. et al., "Anti-obesity effects of green tea: from bedside to bench," Mol. Nutr. Food Res., vol. 50, pp. 176-187 (2006).
Yang, P. et al., "The anti-angiogenic activity of sweet leaf tea extract is mediated by the down-regulation of bFGF and VEGF receptors," an abstract and poster accepted for the American Association for Cancer Research annual meeting, Apr. 18-22, 2009, Denver, Colorado.
Zheng, G. et al., "Anti-obesity effects of three major components of green tea, catechins, caffeine, and theanine in mice," In Vivo, vol. 18, pp. 55-62 (2004).
Zhou, W.-H. et al., "A new sweet diterpene glucoside in leaves of *Rubus suavissimus*,"Acta Botanica Sinica, vol. 34, pp. 315-318 (1992).

* cited by examiner

NATURAL COMPOSITION TO DECREASE EFFECTS OF A HIGH FAT DIET

This is a divisional of co-pending application Ser. No. 12/761,798, filed Apr. 16, 2010, which claims the benefit of provisional application Ser. No. 61/170,341, filed Apr. 17, 2009.

This invention pertains to the use of a combination of natural compounds, specifically, gallic acid, ellagic acid, and rubusoside, which are orally bioavailable, are significant inhibitors of angiogenesis, and can reduce body weight gain, cholesterol, and fat accumulation in mammals on a high fat diet.

Angiogenesis

In an adult, two types of blood vessels can potentially be found. The normal blood vessel is a resting, quiescent, fully developed vessel. A second form, a proliferating or developing blood vessel, occurs rarely during the normal life cycle (only in early development and reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation, capillary differentiation, and anastomosis. All detectable solid tumors (tumors over 2 mm in diameter) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene in neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4), specific inhibitors of endothelial cell growth (e.g., TNP-470, thalidomide, interleukin-12), agents that neutralize pro-angiogenic molecules (e.g., antibodies to fibroblast growth factor (FGF or basic FGF or bFGF) or vascular endothelial growth factor (VEGF)), suramin and its analogs, tecogalan, agents that neutralize receptors for pro-angiogenic factors (e.g., the VEGF receptor FLK-1), agents that interfere with vascular basement membrane and extracellular matrix (e.g., metalloprotease inhibitors, angiostatic steroids), and anti-adhesion molecules (e.g., antibodies such as anti-integrin alpha v beta 3). See L. Rosen, "Antiangiogenic strategies and agents in clinical trials," Oncologist, vol. 5, supplement 1, pp. 20-27 (2000).

Abnormal angiogenesis occurs when improper control of angiogenesis causes either excessive or insufficient blood vessel growth. Excessive blood vessel proliferation favors tumor growth and development of distant metastases, blindness, skin disorders such as psoriasis, and rheumatoid arthritis. Diseases or conditions that have been associated with undesired excessive vascularization include, for example, diabetic retinopathy, retinopathy of prematurity, corneal graft rejection, neovascular glaucoma, retrolental fibroplasia, epidemic keratoconjunctivits, Vitamin A deficiency, atopic keratitis, contact lens overwear, superior limbic keratitis, pterygium keratitis sicca, sjogren's syndrome, acne rosacea, phylectenulosis, syphilis, myobacterial infections, lipid degeneration, chemical bursn, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, radial keratotomy, macular degeneration, sickle cell anemia, sarcoidosis, pseudoxanthoma elasticum, Paget's disease, vein occlusion, carotid obstructive disease, chronic uveitis, chronic vitritis, Lyme's disease, Eales' disease, Behcet's disease, myopia, optic pits, Stargardt's disease, pars planitis, chronic retinal detachment, hyperviscosity syndromes, toxoplasmosis, post-laser complications, abnormal proliferation of fibrovascular or fibrous tissue, hemangiomas, Osler-Weber-Rendu disease, solid tumors, blood borne tumors, acquired immune deficiency syndrome, ocular neovascular disease, age-related macular degeneration, osteoarthritis, diseases caused by chronic inflammation, Crohn's disease, ulceritive colitis, tumors of rhabdomyosarcoma, tumors of retinoblastoma, tumors of Ewing's sarcoma, tumors of neuroblastoma, tumors of ostteosarcoma, leukemia, psoriasis, atherosclerosis, pemphigoid, infections causing retinitis or choroiditis, presumed ocular histoplasmosis, Best's disease, proliferative vitreoretinopathy, Bartonellosis, acoustin neuroma, neruofibroma, trachooma, pyogenic granulomas, obesity, corneal neovascularization, malignant tumor growth beyond 2 mm, benign tumors, benign functional endocrine tumors, arterial/venous malformations, primary hyperparathyroidism, secondary hyperparathyroidism, and tertiary hyperparathyroidism. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," Br. J. Dermatol., vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm without a blood supply to provide nutrients and remove cellular wastes. Tumors in which angiogenesis is important include solid tumors, and benign tumors including acoustic neuroma, neurofibroma, trachoma, and pyogenic granulomas Inhibiting angiogenesis could halt the growth and potentially lead to regression of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemia, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemia and multiple myelomas.

Anti-angiogenic factors inhibit tumor growth beyond 2 mm by inhibiting the angiogenic response and thus inhibiting blood vessel growth to the tumor. Although angiogenesis in a tumor may begin at an early stage, a tumor requires a blood supply to grow much beyond about 2 mm. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 mm$^3$ can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 mm$^3$ may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

Angiogenesis has also been implicated in obesity. Several mice strains, both young and aged animals, used as obesity models treated with anti-angiogenic agents lost weight. See M. A. Rupnick et al., "Adipose tissue mass can be regulated through the vasculature," PNAS, vol. 99, pp. 10730-10735 (2002). This same study also found that adipose tissue mass was reduced by the anti-angiogenic compounds.

Many of the anti-angiogenic agents under development are single compounds and most are synthetic compounds. Disadvantages of a single, synthetic compound can include difficulties in solubility, absorption, bioavailability, toxicity, and drug resistance. These disadvantages are less problematic when a mixture of natural products is used. More importantly, multiple components have the potential to synergistically increase activity, a potential that is unavailable when only a single compound is used.

Chinese Blackberry, *Rubus suavissimus* S. lee

*Rubus suavissimus* S. Lee, a perennial shrub which is called "Chinese blackberry" or "Chinese sweet tea" or "Chinese sweet leaf tea," is one of some 62 species in the genus *Rubus* of the Rosaceae family. It is widely distributed in the southwest of China but flourishes in Guangxi Autonomous Region. Leaves of Chinese blackberry have long been used in southern China as a tea due to its sweet taste, and thus the Chinese name "Tiancha" or "Sweet Leaf Tea." Leaves of the Chinese blackberry contain hundreds of compounds. Among them are gallotannins such as gallic acid and analogues, ellagitannins such as ellagic acid and analogues, flavonol glycosides (rutin and its analogues), and the characteristic sweetening compounds diterpene glycosides (rubusoside and its analogues such as steviol monoside). The sweet taste is due to the presence of the dipterpene glucosides in the leaves, especially rubusoside which can reach a concentration of over 5% (w/w). See T. Tanaka et al., "Rubusoside ($\beta$-D-glucosyl ester of 13-O-$\beta$-D-glucosyl-steviol), a sweet principle of *Rubus chingii* Hu (Rosaceae)," Agric. Biol. Chem., vol. 45, pp. 2165-2166 (1981); and T. Seto et al., "$\beta$-Glucosyl esters of 19$\alpha$-hydroxyursolic acid derivatives in leaves of *Rubus* species," Phytochemistry, vol. 23, pp. 2829-2834 (1984). There are other diterpene glucosides found in the leaves, e.g., suavioside A and suaviosides B, $C_1$, $D_2$, F, G, H, I, and J. See S. Hirono et al., "Sweet and bitter diterpene-glucosides from leaves of *Rubus suavissimus*," Chem. Pharm. Bull., vol. 38, pp. 1743-1744 (1990); W.-H. Zhou et al., "A new sweet diterpene-glucoside in leaves of *Rubus suavissimus*," Acta Botanica Sinica, vol. 34, pp. 315-318 (1992); and K. Ohtani et al., "Minor diterpene glycosides from sweet leaves of *Rubus suavissimus*," Phytochemistry, vol. 31, pp. 1553-1559 (1992). Further chemical analyses of the leaves of thirty-nine other *Rubus* spp. revealed that the presence of diterpene glycosides is only limited to the leaves of *R. suavissimus* and *R. chingii*, whereas glucosyl 19$\alpha$-hydroxyuresana-type triterpenes are more common as constituents in the leaves of *Rubus* spp. in general. See F. Gao et al., "19$\alpha$-hydroxyursane-type triterpene glucosyl esters from the roots of *Rubus suavissimus* S. Lee," Chem. Pharm. Bull., vol. 33, pp. 37-40 (1985).

In China, the leaves of *R. suavissimus* are used not only as tea and a food additive, but also as herbal medicines thought to treat type 2 diabetes, nourish the kidneys, and lower blood pressure. See P.-F. Huang et al., "Comprehensive utilization of *Rubus suavissimus* S. Lee," Guangxi Huagong, vol. 31, pp. 24-25 (2002). The leaf of Chinese blackberry has also been said to help with fever, to relieve stress on the lungs, to reduce the secretion of phlegm, and to relieve coughs. See Y. Ono, "The health beneficial effects of Tien-cha (*Rubus suavissimus* tea) and its applications," Food Style 21, vol. 6, pp. 77-80 (2002). Recent studies indicated an anti-inflammatory and anti-allergy effect. See U. Kotaro, "Antiallergy action of *Rubus suavissimus*," Shokuhin Kogyo, vol. 40, pp. 52-59 (1997); K. Nakahara, "Anti-allergic activity of Tiencha and oolong tea polyphenols," Food Style 21, vol. 2, pp. 45-49 (1998); and K. Nakahara et al., "Anti-allergic composition containing GOD-type ellagitannin as active ingredient," European Patent Application No. 727218 (1996).

An extract of Chinese sweet leaf tea was shown to inhibit angiogenesis, and gallic acid in the extract was identified as partially responsible for the anti-angiogenic activity. See Z. Liu et al., "Gallic acid is partially responsible for the antiangiogenic activities of *Rubus* leaf extract," Phytother. Res., vol. 20, pp. 800-813 (2006); and U.S. Published Patent Application 2007/0031332. Other studies demonstrated a Chinese sweet leaf tea extract inhibited both NF-κB and α-amylase, which are closely related to glucose metabolism. See D. Liu et al., "Bioassay-guided fractionation of *Rubus suavissimus* leaf extracts possessing NF-κB inhibitory activities and a separable cytotoxicity," Pharm. Biol., vol. 43, pp. 713-717 (2005), and H. Li et al., "Rubusiviis A-F, monomeric and oligomeric ellagitannins from Chinese sweet tea and their α-amylase inhibitory activity," Chem. Pharm. Bull., vol. 55, pp. 1325-1331 (2007).

Green tea (*Camellia sinensis*) has long been a popular ingredient in either food or the pharmaceutical industry. Green tea has been proposed for various pharmacological functions, including improvement of insulin sensitivity and glucose tolerance, anti-cancer efficacy, and anti-inflammation. In addition, green tea has been extensively studied for the prevention of metabolic syndrome by stimulating fat oxidation and increasing energy expenditure. The role of green tea in weight loss has been mainly attributed to the presence of catechins, such as the (−)-epigallocatechin-3-gallate (EGCG), (−)-epigallocatechin (EGC), (−)-epicatechin-3-gallate (ECG), and (−)-epicatechin (EC), or to the synergy between catechins and caffeine. See S. Wolfram et al., "Antiobesity effects of green tea: from bedside to bench," Mol. Nutr. Food Res., vol. 50, pp. 176-187 (2006); F. Thielecke et al., "The potential role of green tea catechins in the prevention of metabolic syndrome—a review," Phytochem., vol. 70, pp. 11-24 (2009); and G. Zheng et al., "Anti-obesity effects of three major components of green tea, catechins, caffeine, and theanine in mice," In Vivo, vol. 18, pp. 55-62 (2004).

We have shown that the combination of gallic acid, ellagic acid, and rubusoside can inhibit angiogenesis by inhibition of several pro-angiogenic factors. We have also shown that these three compounds are orally bioavailable and absorbed from the intestine. The ratio of the three compounds used in the experiments was a weight ratio of approximately 1:1.7:17.0 of gallic acid, ellagic acid, and rubusoside, respectively, resulting in a composition with 5% w/w gallic acid, 9% w/w ellagic acid, and 86% w/w rubusoside. This composition was also shown to reduce weight gain, fat accumulation, and cholesterol in rats fed a high fat diet. In addition, it reduced serum triglycerides and slightly reduced glucose in rats fed either a normal or high fat diet. This three-compound composition ("GER") can be used to treat diseases associated with angiogenesis and to decrease weight gain and improve the lipid profiles in mammals on a high fat diet.

EXAMPLE 1

Materials and Methods

Reference Standards.

Gallic acid, rutin, and ellagic acid were purchased from Sigma-Aldrich (St. Louis, Mo.). The reference standards of rubusoside and steviol monoside were isolated as previously described in International Published Application WO 2009/126950, and identified by spectral data (UV, MS, $^1$H NMR, $^{13}$C NMR and 2D-NMR). Both rubusoside and steviol monoside have purities greater than 95% by HPLC-PDA analyses based on a peak area normalization method.

Extracts.

Figure 1:
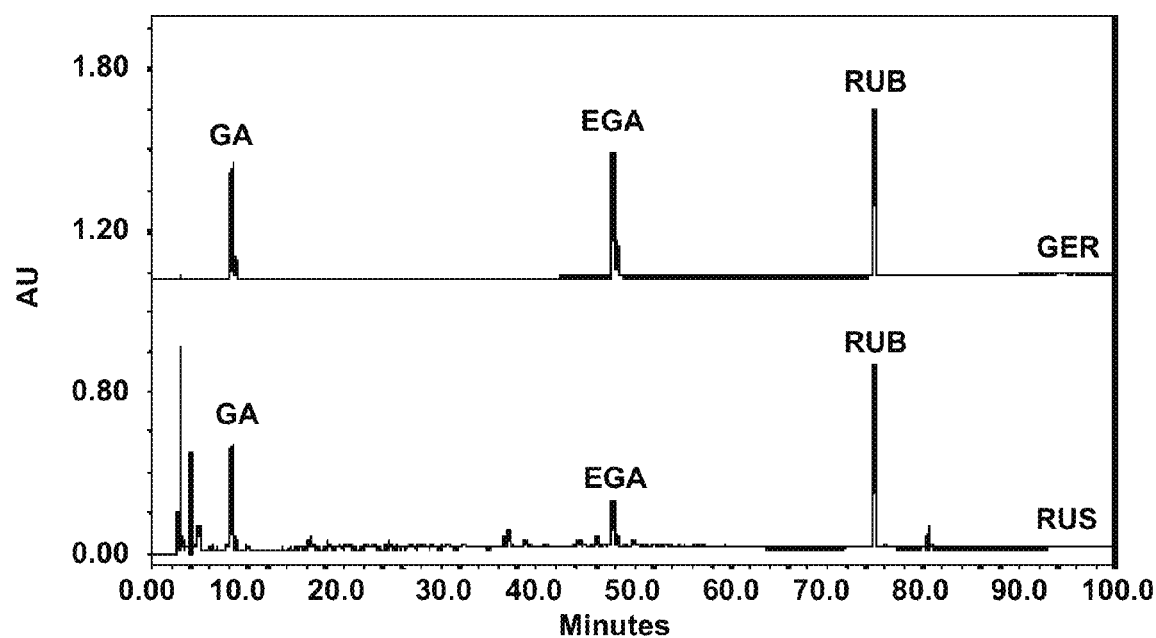
FIG. 1 illustrates the chromatographic fingerprint of the three-compound composition (GER) composed of gallic acid (GA), ellagic acid (EGA), and rubusoside (RUB) in comparison with the chromatographic fingerprint of the standardized extract of Chinese sweet leaf tea, *Rubus suavissimus* (RUS).

A sweet leaf tea extract (RUS) was prepared from the leaves of the sweet leaf tea plant (*Rubus suavissimus* S. Lee). Dried sweet leaves were extracted with hot water to obtain a crude water extract. The crude extract was purified using a chromatographic column containing macroporous adsorbent resin to yield the purified extract (RUS) as the study agent. RUS was previously shown to have an anti-angiogenic potency of total inhibition at 0.1% w/v. See U.S. Published Patent Application 2007/0031332. A chromatographic fingerprint of RUS is shown in FIG. 1. The chromatogram was developed on an HPLC, which showed peaks that were identified as gallic acid, ellagic acid, rutin, rubusoside, steviol monoside, and other compounds. The chromatography was performed by HPLC (Waters 600E system with an auto sampler and a photodiode array detector). The analysis was conducted on a Prevail C18 (5 µm) column 150 mm×4.6 mm. Mobile phase A consisted of HPLC grade acetonitrile; mobile phase B consisted of HPLC-grade water contained 0.3% phosphoric acid. The gradient eluting mobile phase was 0 to 5 min, A/B (3:97, v/v) to A/B (3:97, v/v), 5 to 65 min, A/B (3:97, v/v) to A/B (30:70, v/v), 65 to 85 min, A/B (30:70, v/v) to A/B (60:40, v/v), 85 to 90 min, A/B (60:40, v/v) to A/B (70:30, v/v). Mobile phase was pumped at 0.8 mL/min, the column temperature was 25° C., and the injection volume was 10.0 µL. the wavelength of the PDA detector ranged from 200 to 400 nm and detected at 254 nm, 205 nm and 254+205 nm. Peaks were identified as gallic acid, ellagic acid, rutin, rubusoside, and steviol monoside.

Figure 2:
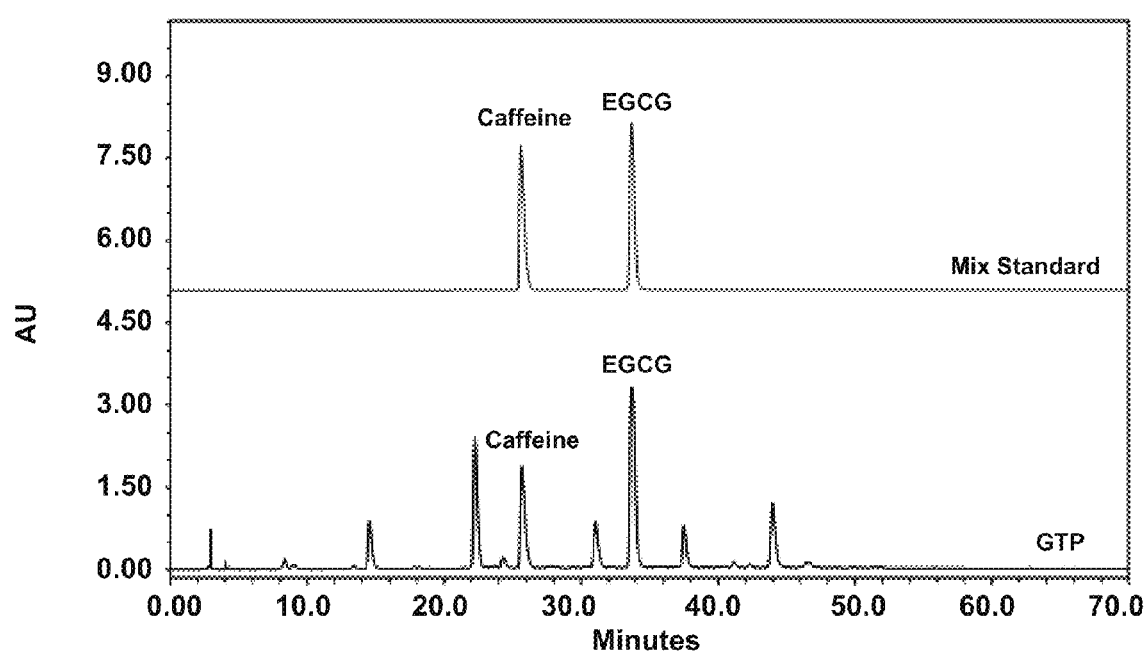
FIG. 2 illustrates the chromatographic fingerprints of the green tea powder (GTP) and a mixture of caffeine and (−)-epigallocatechin-3-gallate (EGCG).

Quantitative analyses established that the amount of gallic acid, ellagic acid, and rubusoside in the RUS extract were 1.38% w/w, 2.40% w/w, and 23.42% w/w, respectively, in a weight ratio of 1:1.7:16.8. The compounds of gallic acid, ellagic acid and rubusoside accounted for only 27% of RUS by weight. A powder consisting of gallic acid, ellagic acid, and rubusoside at the weight ratio of approximately 1:1.7:17.0 was made. This composition of the three compounds contained 5% w/w gallic acid, 9% w/w ellagic acid, and 86% w/w rubusoside and was labeled as "GER." The green tea powder extract was provided courtesy of Amax Nutrasource (Eugene, Oreg.). The major components in the green tea extract were identified by HPLC to be 8.97% caffeine and 36.67% catechins, of which 16.5% was EGCG. (FIG. 2).

Animals.

Male normal Sprague-Dawley (SD) rats (3-6 week old) were purchased from Harlan (Harlan, Indianapolis, Ind.). Male obese-prone SD rats (4-6 week old) were purchased from Charles River (Charles River Laboratories International Inc., Wilmington, Mass.). Animals were housed individually in stainless steel cages in an air-conditioned room at 21° C.±2° C., 50-60% relative humidity, and 12/12 h light/dark cycle. Prior to euthanization, urine was collected from each rat through an individual metabolic cage (Lab Products Inc, Seaford, Del.). Blood or serum was collected via cardiac puncture. All procedures were performed under the approved protocols by the Institutional Animal Care and Use Committee of Louisiana State University (LSU-IACUC), Baton Rouge, La., USA.

Diets.

An AIN-93G purified liquid food was purchased from Dyets Inc. (Bethelem, Pa.) and prepared at a concentration of 0.1755 g/mL with tap water. A normal rat chow (Purina 5001 Lab Diet) was purchased from PMI Nutrition International (Brentwood, Mo.), and a high-fat rat chow was obtained from Research Diets Inc. (New Brunswick, N.J.).

Oral Absorption of the Chinese Sweet Leaf Tea (RUS) in Rats.

Thirty-two normal male SD rats were used in the experiment. Prior to treatment, all rats were fasted overnight. The treated group (n=24) received the RUS extract at a dose of 1 g/kg of body weight (0.1% w/w), and the control group (n=8) received the same volume of water via daily gavage for 3 consecutive days. All rats were given free access to food and water after the gavage. Urine was collected cumulatively for 24 hours on the third day after treatment began.

Anti-Obesity Effect of RUS and GER in Rats on Normal Diets.

Twenty-five normal SD rats were randomly divided into 3 groups. Group 1 (n=8) received a daily dose of 0.5 g/kg-body wt of Chinese sweet leaf tea extract (RUS) in liquid food; group 2 (n=8) received a daily dose of 0.14 g/kg-body wt; equivalent to 0.5 g/kg-body wt RUS) of the three-compound composition (GER) in liquid food; and group 3 (n=9) received only liquid food.

Either RUS or GER was combined with the liquid food. The amount of extract was pre-determined and adjusted based on the body weight of each rat. All rats were given ad libitum access to liquid food for 8 hours (day cycle) after the consumption of extract, and then fasted overnight for 15 hours. The fasting was to increase the hunger of the rats for food the following morning when liquid food carrying RUS or GER was first provided. Body weight was recorded weekly and used to calculate cumulative body weight changes relative to the baseline (%). Food intake was measured daily and relative daily food intake (food consumed/body weight) was calculated. Animals were also observed daily for any abnormal physical and behavioral changes or clinical signs of toxicity, including posture, rough hair coat, decreased responsiveness, and unusual breathing pattern.

Experimental Design for the Rats on High Fat Diets.

Sixty obese-prone SD rats were divided into 4 groups with 15 rats per group. One group was fed normal chow, and the other three groups were fed high-fat chow. Treatments were randomly assigned to each group. Group 1 received a daily dose of the three-compound composition (GER); group 2 received a daily dose of green tea powder (GTP); group 3 was the control on high fat diet (HFD); and group 4 was the control on the normal diet (NCD). The treated rats were first exposed to a small amount of either GER or GTP at the beginning of the experiment to minimize any aversion. GER and GTP were incorporated into the high-fat diet at 3% w/w and 3.5% w/w, respectively. Based on the relative daily food intake as well as the acceptance of extract, daily consumption of these diets was used to attempt to reach target doses of 0.27 g/kg of body weight for GER and 1 g/kg of body weight for GTP. The maximum dose achieved for GER was 0.22 g/kg. All rats were provided ad libitum access to food and tap water throughout the 9-week treatment period. Body weight and food intake were measured weekly. Animals were also observed daily for any abnormal physical and behavioral changes or clinical signs of toxicity.

Blood Glucose Measurements.

Fasting blood glucose was measured at week 0 (baseline), week 4, and week 8 after treatments began. A small drop of blood was drawn from the tail-vein, and glucose was measured with a commercial glucometer (Abbott Laboratories, North Chicago, Ill.) after a 6-hr fasting during the day.

Serum Triglycerides Measurement.

At the end of the study, blood was drawn and the serum separated from the blood cells through centrifugation at 2000×g for 10 min. The serum samples were stored at −20° C. until analysis. Serum triglyceride level was analyzed using a serum triglyceride determination kit (Sigma-Aldrich, St. Louis, Mo.).

Blood Sampling and Clinical Pathology.

At the end of the treatment, all rats were anesthetized with isoflurane and euthanized. Blood samples were collected and examined for possible signs of toxicity or adverse effects resulting from the consumption of either GER or GTP. For the hematology analysis, blood samples were collected in an EDTA vacutainer (Beckin, Dickinson and Company, Franklin Lakes, N.J.). The parameters tested included erythrocytes, hemoglobin, hematocrit, red blood cell distribution width (RDW), mean corpuscular volume (MCV), mean corpuscular hemoglobin (MCH), mean corpuscular hemoglobin concentration (MCHC), platelet count, mean platelet volume (MPV), and total WBCs. Blood chemistry samples were collected in a vacutainer and allowed to coagulate. Serum was separated by centrifugation at 2000×g for 10 min. The serum was then tested for glucose, alanine aminotransferase (ALT), aspartate aminotransferase (AST), alkaline phosphatase (APH), creatine kinase (CK), total bilirubin, total protein, albumin, globulin, total cholesterol, urea nitrogen (BUN), creatinine, calcium, phosphorus, sodium, potassium, chloride, bicarbonate, and anion gap. Both blood and serum samples were stored at $-20°$ C. and immediately submitted to the Louisiana Animal Disease Diagnostic Laboratory (School of Veterinary Medicine, Louisiana State University, Baton Rouge, La.) for the analyses.

Statistical analyses. All data were analyzed with the Statistical Analysis System (SAS, Cary, N.C.). Analysis of variance (ANOVA) with repeated measures was performed on the body weight changes, relative daily food intake, blood glucose levels, and serum triglyceride levels throughout the experimental period. The serum chemistry and hematology data were analyzed using one-way ANOVA. Tukey's post hoc test was performed to compare group differences. All results reported were expressed as mean±SEM, unless otherwise stated.

EXAMPLE 2

Gastrointestinal Absorption of Chinese Sweet Leaf Tea Components

Figure 3:
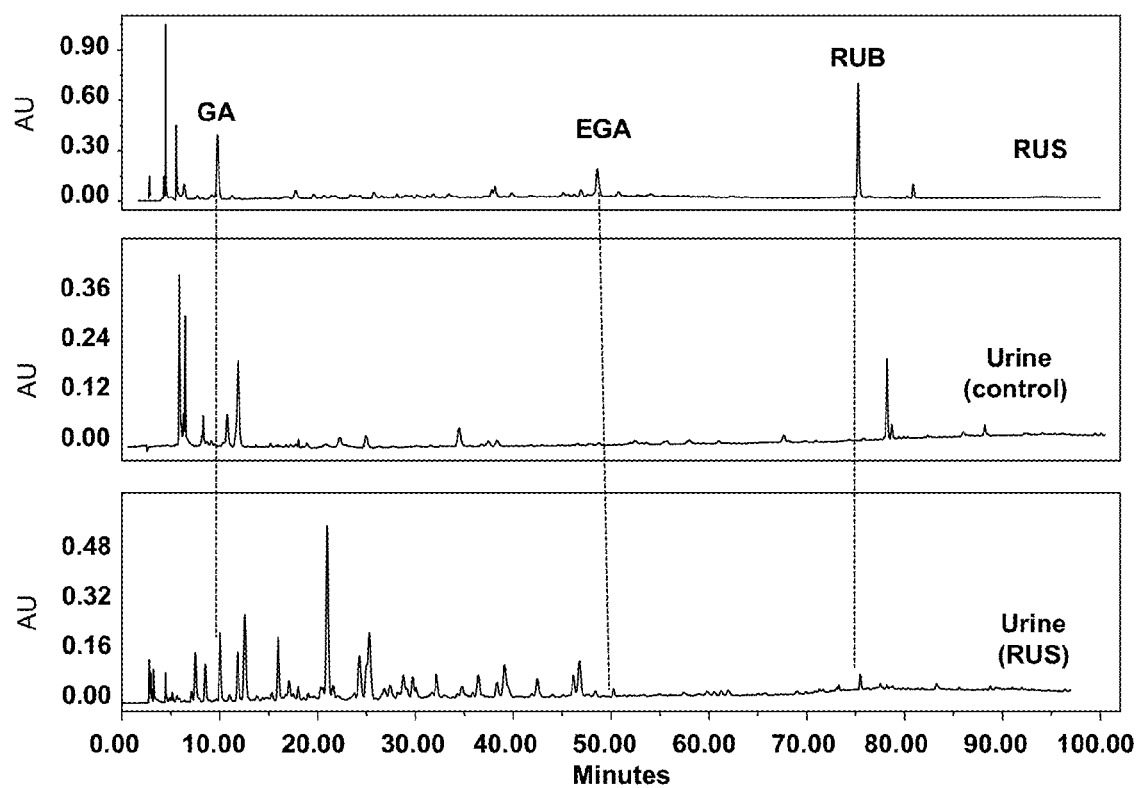
FIG. 3 illustrates the chromatographic fingerprints of the standardized Chinese sweet leaf tea (*Rubus suavissimus*) extract (RUS), control-rat urine (blank diet), and RUS-treated rat urine (24 hr after a single oral administration of 0.5 g/kg via oral gavage), and indicates the presence of the three major marker compounds, gallic acid (GA), ellagic acid (EGA), and rubusoside (RUB).

After a single oral administration of the Chinese sweet leaf tea extract (RUS) a dose of 1.0 g/kg of body weight, only gallic acid, ellagic acid, and rubusoside were detected in the urine of rats after 24 hr (FIG. 3). Noticeably absent in the urine was both rutin and steviol monosides. Gallic acid had the highest absorption rate. Unmetabolized gallic acid in the urine was measured as 91.7 µg, about 4.5% of the 2028 µg orally administered; unmetabolized ellagic acid was measured as 13.3 µg, about 2.2% of the 603 µg orally administered; and unmetabolized rubusoside was measured as 65.3 µg, about 0.3% of the 21808 µg orally administered. Gallic acid, ellagic acid, and rubusoside were thus found to be orally bioavailable.

EXAMPLE 3

Body Weight Gain and Food Intake in Rats on Normal Diets

Figure 4:
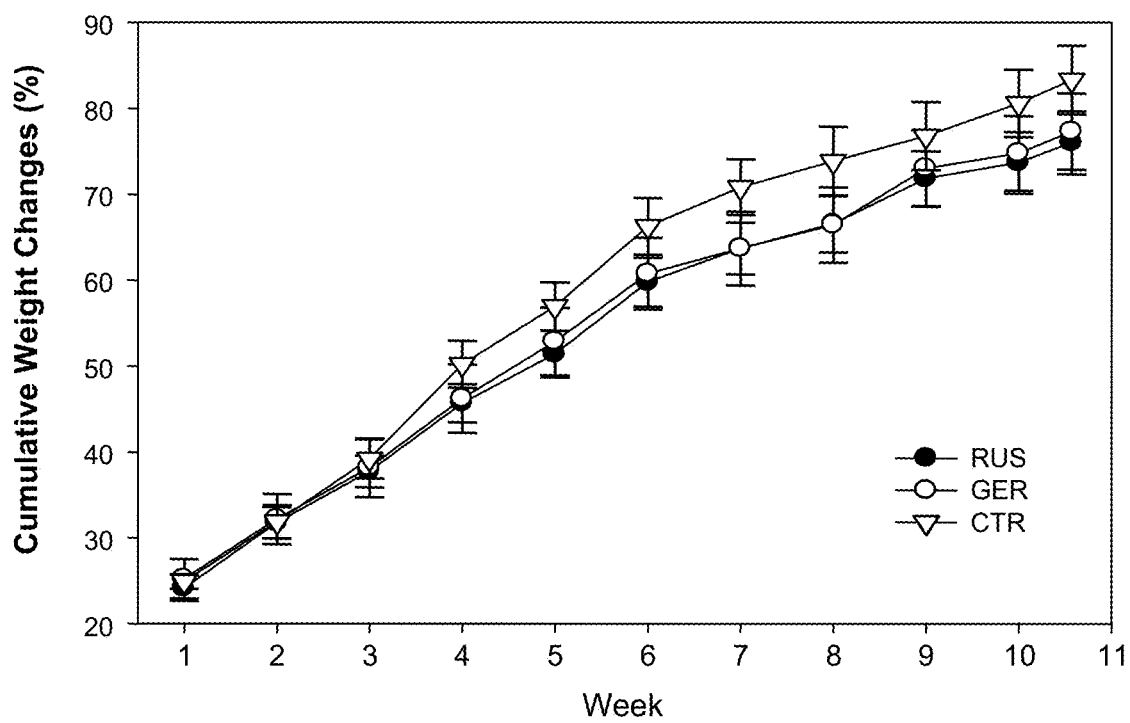
FIG. 4 illustrates the effects of the standardized Chinese sweet leaf tea (*Rubus suavissimus*) (RUS) (0.5 g/kg-body wt/day) and the three-compound composition (GER) (0.14 g/kg-body wt/day) as compared to the control rats (CTR) on the cumulative body weight changes (%) in male rats fed with normal diet for 11 weeks. Vertical bars at each data point represent one unit of standard error of the mean (n=8 for RUS and GER group; n=9 for CTR group).

Deviation in body weight gain of both RUS and GER treatments from the control group began about 3 weeks after daily consumption of the extracts (FIG. 4). The body weight at week 6 as compared with the HFD control was about 6.71% less for the RUS group and 6.02% less for the GER group. However, these differences were not statistically significant. Food intake was not affected by either RUS or GER treatment, and each animal daily consumed approximately 5% of their body weight.

EXAMPLE 4

Body Weight Gain and Food Intake in Diet-Induced Obese Rats

Figure 5A:
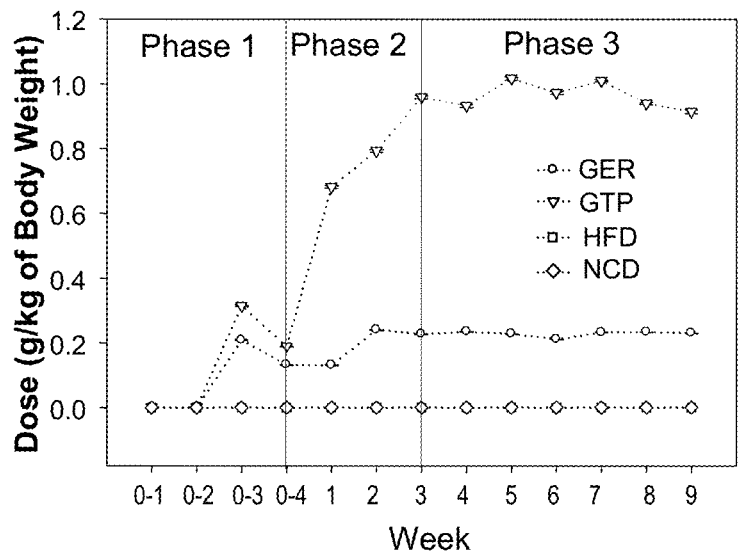
FIG. 5A illustrates the average oral intake (% w/w) of the three-compound composition (GER) and green tea (*Camellia sinensis*) powder (GTP) extract in the diet-induced obese rats.
Figure 5B:
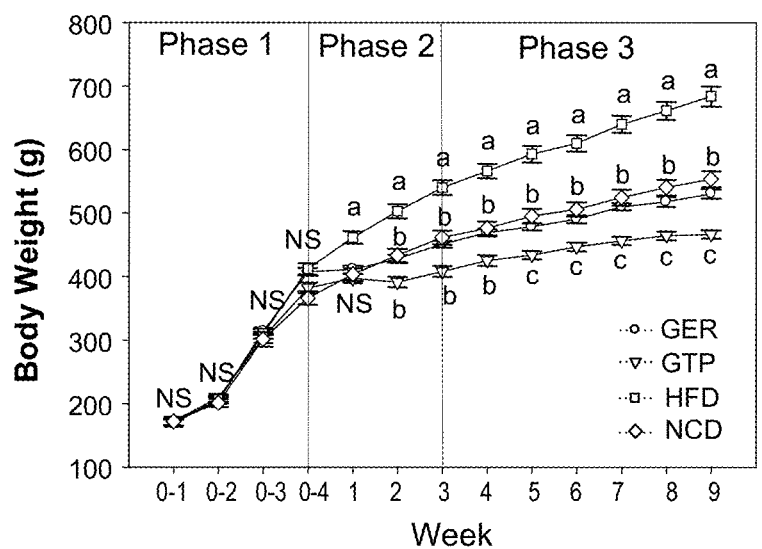
FIG. 5B illustrates the effects of oral GER and GTP on the body weight of diet-induced obese rats (fed high fat diet) as compared to the control groups receiving either high fat (HFD) or normal (NCD) diet. All data were expressed as the mean±standard error where n=15. Different letters at each week indicate a significant difference at $p \leq 0.05$.

The effects of GER and GTP were tested in obese prone rats given a high fat diet. The experimental results were presented in three phases based on the amount of either GER or GTP consumed as shown in FIG. 5A. In phase 1, when the rats were being acclimated to the taste of GER or GTP, the rats consumed 0.2 g/kg and 0.3 g/kg of GER and GTP, respectively. During this phase, neither GER nor GTP consumption affected the weight gain or food intake. In Phases II and III, GER or GTP was incorporated into the high-fat chow diet, which was the only food source for these rats. In phase 2, until week 3, a significant increase in the GTP consumption was observed. During phase 2, significant reduction in the body weight of the GER and GTP groups over the HFD control were observed beginning at week 3, and the body weights were similar to that of the NCD group (normal diet control). GTP was the most effective in reducing the gain in body weight. At week 5, the GTP group showed a body weight reduction of 27% ($p \leq 0.001$) and 12% ($p=0.0081$) as compared to the HFD and NCD controls, respectively. The reduction in body weight gain in the GER and GTP groups continued after week 5, but at slower rates. At 9 weeks, the end of the treatment, body weight was reduced by 22% ($p \leq 0.001$) with the consumption of 0.22 g/kg GER and by 32% ($p \leq 0.001$) with consumption of 1.0 g/kg GTP consumption as compared to the HFD control (FIG. 5B). The body weight of the GER and NCD groups were similar. No difference in food intake was observed among the three groups on the high-fat diet (GER, GTP and HFD). Overall, the groups on the high-fat diet had a daily food intake of about 4% body weight, and the group on a normal diet had a daily food intake of about 6% body weight over the 9 week treatment period. Although there was a significant difference in the amount of food intake between the food types (normal or high-fat diet), the total calorie intake was the same.

EXAMPLE 5

Abdominal Fat Accumulation in Diet-Induced Obese Rats

Liver, kidneys, mesentery, epididymal, retroperitoneal, and perirenal adipose pads of the experimental rats were collected and weighed. Total abdominal fat (epididymal, retroperitoneal, and perirenal) was reduced in the NCD, GER, and GTP groups by 57%, 48%, and 70%, respectively, as compared to the HFD group (Table 1). The fat mass reduction was mainly due to a decrease in the retroperitoneal and perirenal adipose pads. Mesentery fat in the NCD, GER, and GTP groups was also significantly reduced by 48%, 56%, and 74%, respectively, as compared to the HFD group. The GTP group, overall, had the least abdominal fat. The GER and NCD groups showed similar fat accumulation. The liver and kidney weights of the GER and GTP groups were not significantly different from that of the HFD group. However, the liver and kidneys in the NCD group were slightly heavier than the groups on high-fat diet, possibly a function of the relatively lower disemboweled body weight in the NCD group.

TABLE 1

Effects of the three-compound composition (GER) and green tea (Camellia sinensis) powder (GTP) on the weight (% w/w of disemboweled body weight (DBW)) of organs and abdominal adipose tissues of diet-induced obese SD rats compared to the control groups receiving high fat (HFD) or normal diet (NCD).

| Relative Organs/Tissues Weight (% w/w) | Group | | | |
|---|---|---|---|---|
| | HFD | NCD | GER | GTP |
| Liver | $2.95 \pm 0.17^b$ | $3.52 \pm 0.23^a$ | $2.87 \pm 0.06^b$ | $2.81 \pm 0.21^b$ |
| Kidneys | $0.54 \pm 0.04^c$ | $0.71 \pm 0.03^a$ | $0.62 \pm 0.01^b$ | $0.65 \pm 0.04^b$ |
| Mesentery with Fat | $3.77 \pm 0.71^a$ | $1.95 \pm 0.44^b$ | $1.66 \pm 0.07^b$ | $0.99 \pm 0.21^c$ |
| Total Abdominal Fat | $10.07 \pm 1.50^a$ | $4.37 \pm 0.88^b$ | $5.28 \pm 0.26^b$ | $3.03 \pm 0.73^c$ |
| Epididymal | $3.90 \pm 0.46^a$ | $1.90 \pm 0.40^b$ | $2.18 \pm 0.10^b$ | $1.42 \pm 0.25^c$ |
| Retroperitoneal | $4.45 \pm 0.93^a$ | $1.66 \pm 0.38^c$ | $2.27 \pm 0.13^b$ | $1.15 \pm 0.37^c$ |
| Perirenal | $1.71 \pm 0.30^a$ | $0.81 \pm 0.16^b$ | $0.83 \pm 0.04^b$ | $0.46 \pm 0.14^c$ |

All values are expressed as mean ± standard error where n = 15. Different letters in each row indicated a significant difference at $p \leq 0.05$

EXAMPLE 6

Fasting Blood Glucose in Diet-Induced Obese Rats

Figure 6:
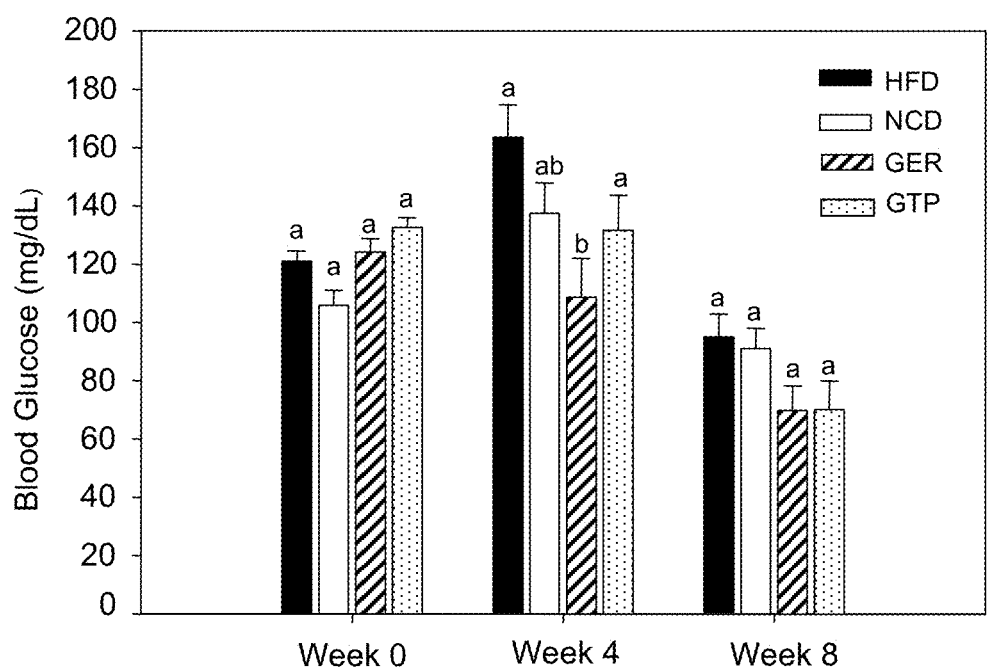
FIG. 6 illustrates the effects of the three-compound composition (GER) and green tea (*Camellia sinensis*) powder (GTP) on the blood glucose levels (mg/dL) of the diet-induced obese rats measured at Week 0 (baseline), Week 4, and Week 8 of treatment as compared to the control groups receiving either a high fat (HFD) or normal (NCD) diet. All data are expressed as the mean±standard error where n=15. Different letters on each week indicate a significant difference at $p \leq 0.05$.

Blood glucose was measured after a 6-hr fasting period during the day. Using as a baseline the glucose levels prior to treatment (week 0), the blood glucose level was significantly lowered by 12% (p=0.001) as compared to the HFD group after 4 weeks of oral administration of GER (FIG. 6). GTP also showed a small, but insignificant blood glucose lowering effect. Both GER and GTP tended to lower the blood glucose in week 8, but neither was statistically significant.

EXAMPLE 7

Serum Triglycerides in Diet-Induced Obese SD Rats

The serum triglyceride levels of the HFD, NCD, GER, and GTP groups were measured to be 168±18 mg/dL, 200±30 mg/dL, 89±17 mg/dL, and 80±11 mg/dL, respectively. A pronounced effect of both GER and GTP was seen with almost a 50% reduction in serum triglycerides. Surprisingly, the serum triglyceride level of the NCD group, which was on a normal low-fat diet, was not significantly different from the HFD group, even though the body weight gain was significantly less.

EXAMPLE 8

Toxicology Related to Treatments

Oral administration of RUS and GER were previously well-tolerated in the normal SD rats for the entire 10-week experiment (data not shown). No clinical signs of toxicity or abnormal behavior were observed in either the normal rats or the obese-prone rats after a 9-week administration of either GER or GTP. Animals in the GTP group appeared to be more physically active than the other groups based on daily observations. There were no treatment-related adverse effects observed in either the hematological (data not shown) or blood chemistry data (Table 2). Elevated values of CK were observed in all groups with high variation in measurements. The total cholesterol level was significantly lower in the NCD, GER and GTP groups as compared to the HFD group, by approximately 40%, 20% and 15%, respectively. Although the BUN and creatinine levels in the GTP group were slightly different from the NCD or HFD group, the values were within the normal range of 11-17 mg/dL for BUN and 0.4-0.7 mg/dL for creatinine See Clinical Laboratory Parameters for Crl:CD (SD) Rats, information prepared by Mary L. A. Giknis, Ph.D., and Charles B. Clifford, D. V. M., Ph.D., March 2006, Charles River Laboratory, Wilmington, Mass. No other abnormal values were noted.

TABLE 2

Effects of the purified Chinese sweet leaf tea (Rubus suavissimus) extract (GER) and green tea (Camellia sinensis) powder (GTP) on the serum chemistry values of diet-induced obese rats compared to the control groups receiving high fat (HFD) or normal diet (NCD).

| | Groups | | | |
|---|---|---|---|---|
| | HFD | NCD | GER | GTP |
| Glucose (mg/dL) | $196.80 \pm 13.36$ | $216.10 \pm 13.90$ | $206.89 \pm 16.31^{***}$ | $172.50 \pm 10.89^{\dagger}$ |
| AST (IU/L) | $142.78 \pm 16.08^{*}$ | $194.89 \pm 41.82^{*}$ | $206.44 \pm 32.64$ | $168.57 \pm 28.48^*$ |
| ALT (IU/L) | $39.44 \pm 2.14^{***}$ | $51.86 \pm 3.84^*$ | $45.22 \pm 4.98$ | $48.57 \pm 2.83^*$ |
| AP (IU/L) | $267.70 \pm 15.35^a$ | $227.90 \pm 7.94^{ab}$ | $205.40 \pm 9.31^b$ | $217.20 \pm 10.83^b$ |
| CK (IU/L) | $3785.33 \pm 1399$ | $2847.50 \pm 1295^{*}$ | $5792.44 \pm 2149^{*}$ | $4820.63 \pm 1806^{\dagger}$ |
| Bilirubin (mg/dL) | $0.19 \pm 0.04$ | $0.22 \pm 0.04$ | $0.36 \pm 0.05$ | $0.25 \pm 0.05$ |
| Protein (g/dL) | $5.91 \pm 0.08$ | $5.76 \pm 0.12$ | $5.98 \pm 0.12$ | $5.80 \pm 0.10$ |
| Albumin (g/dL) | $3.12 \pm 0.07$ | $3.12 \pm 0.07$ | $3.31 \pm 0.07$ | $3.24 \pm 0.06$ |
| Globulin (g/dL) | $2.79 \pm 0.06$ | $2.64 \pm 0.06$ | $2.67 \pm 0.06$ | $2.56 \pm 0.06$ |
| Cholesterol (mg/dL) | $103.50 \pm 3.20^{**a}$ | $61.80 \pm 3.30^c$ | $79.90 \pm 4.72^b$ | $84.80 \pm 4.05^b$ |
| BUN (mg/dL) | $17.50 \pm 0.48^{ab}$ | $19.10 \pm 0.43^a$ | $16.40 \pm 0.64^{bc}$ | $14.40 \pm 0.60^c$ |
| Creatinine (mg/dL) | $0.30 \pm 0.00^b$ | $0.31 \pm 0.01^b$ | $0.33 \pm 0.02^{ab}$ | $0.38 \pm 0.02^a$ |

TABLE 2-continued

Effects of the purified Chinese sweet leaf tea (*Rubus suavissimus*) extract (GER) and green tea (*Camellia sinensis*) powder (GTP) on the serum chemistry values of diet-induced obese rats compared to the control groups receiving high fat (HFD) or normal diet (NCD).

| | Groups | | | |
|---|---|---|---|---|
| | HFD | NCD | GER | GTP |
| Calcium (mg/dL) | 10.34 ± 0.15 | 10.26 ± 0.19 | 10.02 ± 0.24 | 9.93 ± 0.19 |
| Phosphorus (mg/dL) | 7.35 ± 0.22 | 8.00 ± 0.50 | 8.18 ± 0.60 | 8.45 ± 0.76 |
| Sodium (mmol/L) | 141.40 ± 0.48 | 141.30 ± 0.75 | 140.70 ± 0.96 | 140.60 ± 0.67 |
| Potassium (mmol/L) | 6.35 ± 0.24 | 6.51 ± 0.39 | 7.39 ± 0.63*** | 6.55 ± 0.42** |
| Chloride (mmol/L) | 100.30 ± 0.47 | 99.90 ± 0.64 | 101.00 ± 0.58 | 100.20 ± 0.59 |
| Bicarbonate(mmol/L) | 23.82 ± 0.45 | 24.28 ± 0.64 | 22.48 ± 0.86 | 22.36 ± 0.96 |
| Anion Gap (mmol/L) | 23.63 ± 0.70 | 23.63 ± 0.91 | 25.13 ± 1.31 | 25.77 ± 1.55 |

All values were expressed as mean ± standard error, n = 10, unless otherwise specified (*n = 7; n = 8; *n = 9). Different letters on each row indicate significant difference, $p \leq 0.05$.

The oral bioavailability of gallic acid, ellagic acid, and rubusoside was shown above. A new formulation that consisted of a combination of gallic acid, ellagic acid, and rubusoside (GER) was tested. The three-compound composition caused similar weight suppressive effect as the standardized extract (RUS) on normal rats. GER significantly reduced the body weight gain of the diet-induced obese rats by 22% and the total abdominal fat accumulation by 48%. The results were similar to those seen in the rats fed a normal diet.

Botanical extracts have been good sources of natural remedies for obesity and green tea is an outstanding example. Both green tea and GER were found to be effective against weight gain and fat accumulation. However, there are advantages to the use of GER. First, GER does not contain either caffeine or EGCG. GER is composed of only gallic acid, ellagic acid, and rubusoside. GTP, with its caffeine and EGCG, may have adverse effects at high doses. Second, the effective dose of GER was shown to be lower than that reported for GTP by a factor of 4.5 fold. GER at the dose of 0.22 g/kg body weight showed a significant anti-obesity effect whereas GTP was used at 1 g/kg of body weight. This difference in dose, if translated to human doses, would mean a 90 kg human would only need to consume 2.8 g GER in solid dose daily, but would need a daily dose of 12.9 g of green tea with contains about 1,161 mg of caffeine (e.g. 26 500 mg-capsules). Third, the production of GER can be better controlled both in terms of dose of active ingredients and safety. Since GER is a combination of only three ingredients, it can be formulated with minimal batch-to-batch variations. Although the major components of the green tea are known, controlling batch-to-batch variations of a complex botanical extract is a challenging task.

EXAMPLE 9

Effects of RUS, GER, and Individual Components on Pro-Angiogenic Growth Factors

The HUVEC assay used human umbilical vein endothelial cells purchased from the American Type Culture Collection (ATCC # CRL-1730, Manassas, Va.). Human umbilical vein endothelial cells (HUVEC) were grown in M199 media containing 20% fetal bovine serum, 30 μg/ml endothelial cell growth supplements, 4 mM L-glutamin, 100 U/ml penicillin, and 100 μg/ml streptomycin. Cells were incubated at 37° C. in a humidified atmosphere of 5% $CO_2$. They were treated with PBS (the vehicle used to dissolve sweet leaf tea extract) and various concentrations of either RUS, GER, gallic acid, rubusoside, or ellagic acid (at various concentrations, from 0 to 100 μg/ml) for 24 hrs. Cells were then lysed with lysis buffer containing 20 mM MOPS, 2 mM EGTA, 5 mM EDTA, 30 mM NaF, 40 mM (3-glycerophosphate, 20 mM sodium pyruvate, 0.5% Triton X-100, and 1 mM sodium orthovanadate with protease inhibitor cocktail (Sigma), and the cell lysates were subjected to protein analysis and western blotting analysis to assess for VEGF (vascular endothelial growth factor), FGF or bFGF (basic fibroblast growth factor), and FLK-1 (a VEGFR2 receptor protein) using the relevant antibodies of VEFG (R&D System), bFGF (Upstate Biotechnology); FLK-1 (Santa Cruz Biotechnology). (See Ma, J. et al., "PTEN regulate angiogenesis through PI3k/AktNEGF signaling pathway in human pancreatic cancer cells," Mol. Cell Biochem., vol. 331, pp. 161-171 (2009); and Sukhthanjar, M., et al., "A green tea component suppresses posttranslational expression of basic fibroblast growth factor in colorectal cancer. Gastroenterology," vol. 134, pp. 1972-1980 (2008)). β-Actin was used as a quality control of the assays. The results are shown in FIGS. 7-12.

Figure 7:
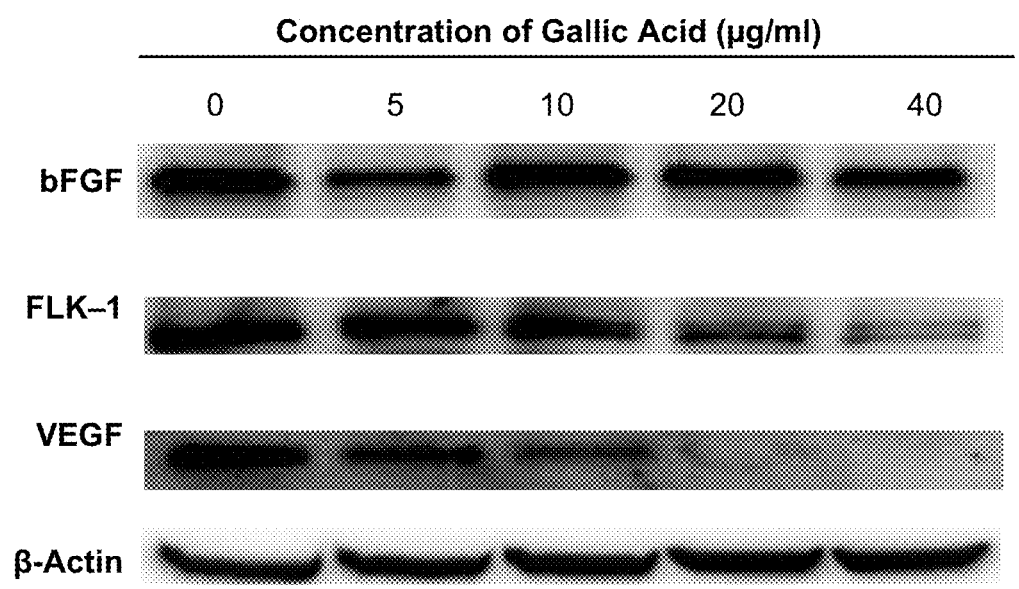
FIG. 7 illustrates the results of a Western blot analysis of cell lysates from HUVEC cells treated with various concentrations of gallic acid (0, 5, 10, 20 and 40 μg/ml) for expression levels of the pro-angiogenic factors, bFGF, FLK-1, and VEGF. β-actin was added as a quality control.
Figure 8:
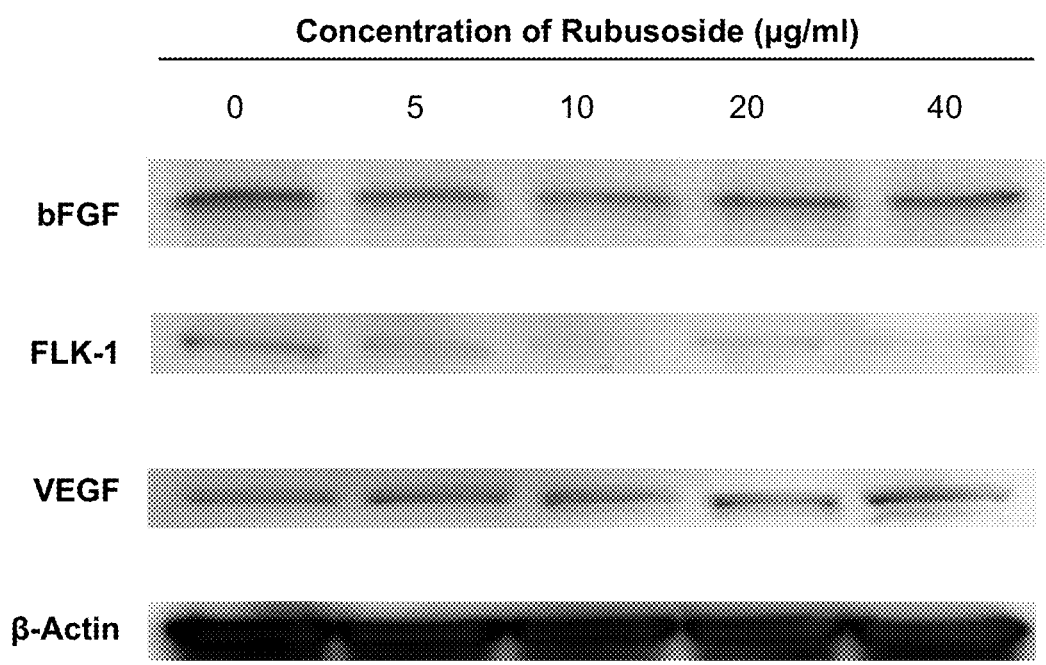
FIG. 8 illustrates the results of a Western blot analysis of cell lysates from HUVEC cells treated with various concentrations of rubusoside (0, 5, 10, 20 and 40 μg/ml) for expression levels of the pro-angiogenic factors, bFGF, FLK-1, and VEGF. β-actin was added as a quality control.
Figure 9:
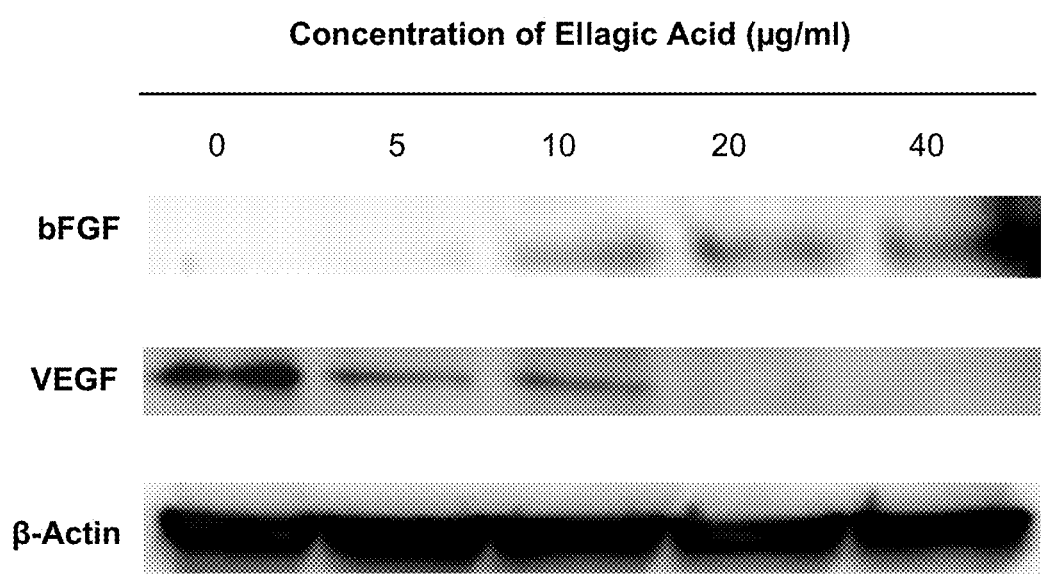
FIG. 9 illustrates the results of a Western blot analysis of cell lysates from HUVEC cells treated with various concentrations of ellagic acid (0, 5, 10, 20 and 40 μg/ml) for expression levels of the pro-angiogenic factors, bFGF, FLK-1, and VEGF. β-actin was added as a quality control.

FIG. 7 shows the effects of gallic acid at various concentrations. Gallic acid alone inhibited the expression of VEGF in a concentration-dependent manner, slightly reduced the expression of FLK-1, but did not suppress the expression of bFGF in concentrations up to about 40 μg/ml. FIG. 8 shows the effects of rubusoside acid at various concentrations. Rubusoside alone reduced the expression of FLK-1, but did not inhibit the expression of either bFGF or VEGF in concentrations up to about 40 μg/ml. FIG. 9 shows the effects of ellagic acid at various concentrations. Ellagic acid alone inhibited the expression of VEGF in a concentration-dependent manner, but did not suppress the expression of bFGF in concentrations up to about 40 μg/ml.

Figure 10:
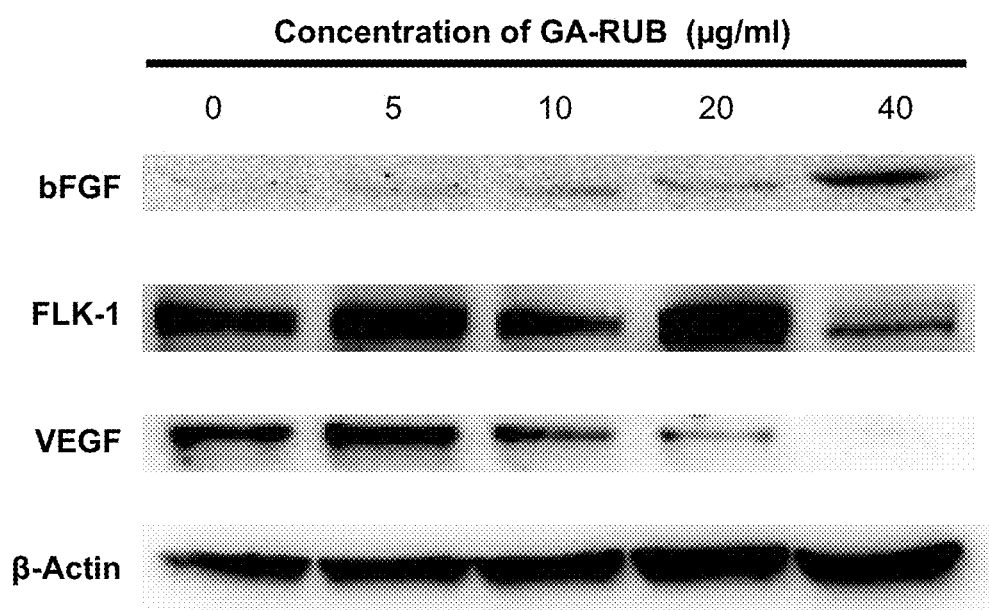
FIG. 10 illustrates the results of a Western blot analysis of cell lysates from HUVEC cells treated with various concentrations of a combination of gallic acid and rubusoside (0, 5, 10, 20 and 40 μg/ml) for expression levels of the pro-angiogenic factors, bFGF, FLK-1, and VEGF. β-actin was added as a quality control.
Figure 11:
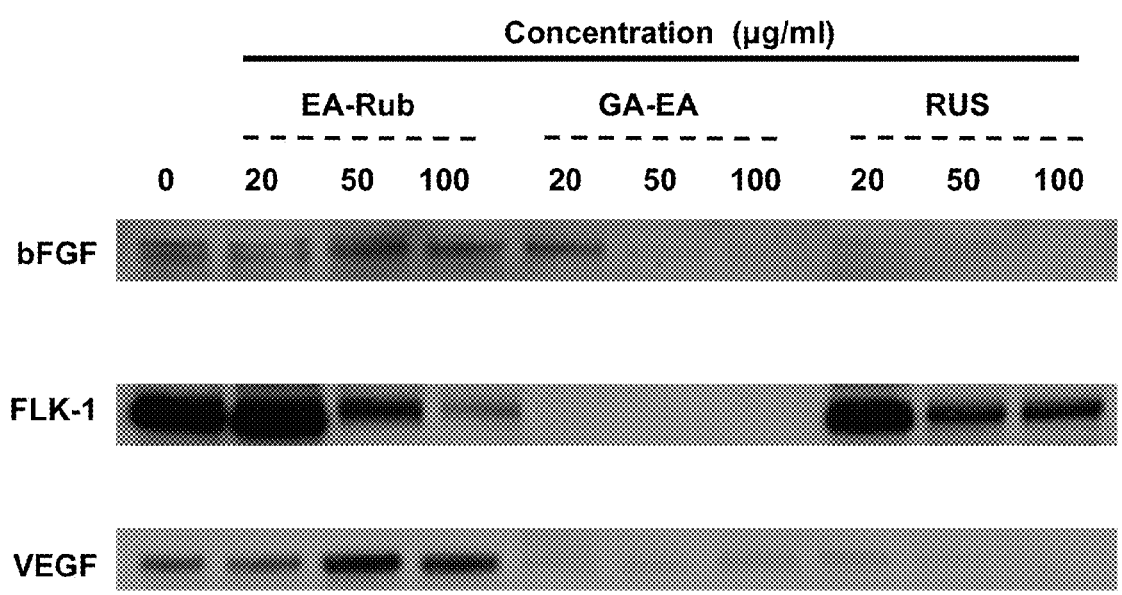
FIG. 11 illustrates the results of a Western blot analysis of cell lysates from HUVEC cells treated with various concentrations of a combination of ellagic acid and rubusoside (0, 20, 50, and 100 μg/ml), a combination of gallic acid and ellagic acid (20, 50, and 100 μg/ml), and the Chinese blackberry extract (RUS) (20, 50, and 100 μg/ml) for expression levels of the pro-angiogenic factors, bFGF, FLK-1, and VEGF. β-actin was added as a quality control.

Various combinations of gallic acid, rubusoside, and ellagic acid were also tried. FIG. 10 shows the results of the combination of gallic acid and rubusoside at a ratio of 1:17.2 w/w. The GA-Rub combination produced similar effects as gallic acid and rubusoside alone. This combination inhibited expression of both VEGF and Flk-1, but did not inhibit the expression of bFGF. FIG. 11 shows the results of the combination of ellagic acid and rubusoside (EA-Rub) at a ratio of 1:9.6 w/w, of gallic acid and ellagic acid (GA-EA) at a ratio of 1:1.8 w/w, and of RUS extract. The EA-Rub combination only inhibited the expression of FLK-1 and had no effect of FGF or VEGF. The GA-EA combination reduced the levels of all three pro-angiogenic factors—bFGF, VEGF, and FLK-1, but the concentrations used were higher up to about 100 μg/ml. The RUS extract reduced the expression of FGF and VEGF, but had only slight inhibition of FLK-1.

Figure 12:
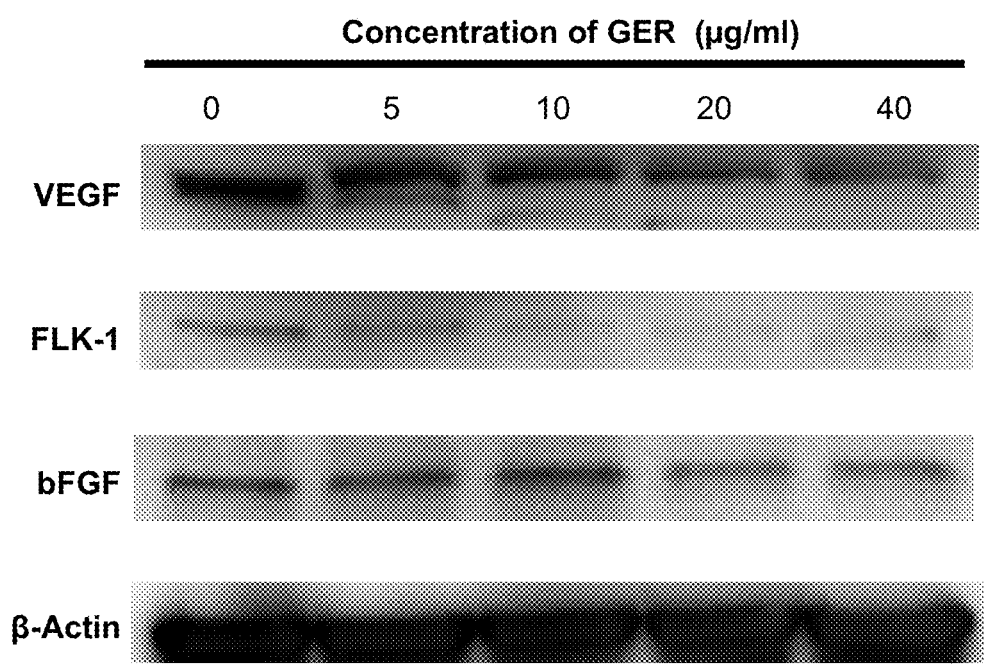
FIG. 12 illustrates the results of a Western blot analysis of cell lysates from HUVEC cells treated with various concentrations of a combination of gallic acid, ellagic acid and rubusoside (GER) (0, 5, 10, 20 and 40 μg/ml) for expression levels of the pro-angiogenic factors, bFGF, FLK-1, and VEGF. β-actin was added as a quality control.

FIG. 12 shows the results of the three-compound combination (GER) on the pro-angiogenic factors. The weight ratio of the three compounds in the composition was approximately 1:1.7:17.0 of gallic acid, ellagic acid, and rubusoside, respectively, resulting in a composition with 5% w/w gallic acid, 9% w/w ellagic acid, and 86% w/w rubusoside. As shown in FIG. 12, GER inhibited all three pro-angiogenic factors, including a strong inhibition of FLK-1 at even 5 µg/ml. In contrast, as shown in FIG. 11, RUS even at 100 µg/ml only slightly inhibited FLK-1.

In summary, gallic acid or ellagic acid alone inhibited the expression of VEGF in a concentration-dependent manner in HUVEC cells. Gallic acid or rubusoside alone or in combination inhibited the expression of the VEGFR2 protein, FLK-1. None of the three compounds alone suppressed the protein level of bFGF in HUVEC cells. The inhibitory effect of ellagic acid on VEGF was decreased when used in combination with rubusoside, but the inhibitory effect of rubusoside on FLK-1 was maintained. When HUVEC cells were treated with the combination of ellagic acid and gallic acid (up to about 100 ug/ml), the levels of all three pro-angiogenic factors (bFGF, FLK-1 and VEGF) were markedly reduced by 80 to 90% over the control, especially the levels of FLK-1 and VEGF. Both RUS and the three-compound combination (GER) inhibited all three pro-angiogenic factors. However, GER had more pronounced inhibitory effect on FLK-1 than RUS. In summary, the two-compound combination of gallic acid and ellagic acid or the three-compound combination (GER) significantly inhibited the expression of the three pro-angiogenic growth factors.

Miscellaneous

The term "effective amount" as used herein refers to an amount of a composition comprising gallic acid, ellagic acid and rubusoside (GER) orally administered and in which the plasma concentration is sufficient to inhibit angiogenesis to a statistically significant degree (p<0.05). The composition consists of gallic acid, ellagic acid, and rubusoside in an amount at least 50% by weight of the composition, more preferable at least 90% by weight, and most preferably 100% by weight. If the composition is liquid, then the composition comprises gallic acid, ellagic acid, and rubusoside in an amount equal to at least about 50% mass percent of dissolved solids. The term "effective amount" therefore includes, for example, an amount sufficient to prevent the growth of angiogenic vessels found in diseases of tumor growth, diabetic retinopathy, psoriasis, retinopathy of prematurity, and preferably to reduce by at least 50%, and more preferably to reduce by at least 90%, the amount of angiogenesis. The dosage ranges for the administration of GER are those that produce the desired effect. Generally, the dosage will vary with the age, weight, condition, sex of the patient or pathology, and the degree of desired angiogenic response. A person of ordinary skill in the art, given the teachings of the present specification, may readily determine suitable dosage ranges. The dosage can be adjusted by an individual physician in the event of any contraindications. In any event, the effectiveness of treatment can be determined by monitoring the extent of angiogenic inhibition or remission by methods well known to those in the field. Moreover, the GER can be applied in pharmaceutically acceptable carriers known in the art. The application can be oral, by injection, or topical.

A therapeutic and stable composition can be delivered by a clear solution for intravenous fusion, injection fluid locally or systematically, and by solid dose via oral administration. Gallic acid, ellagic acid, and rubusoside each is generally regarded as a safe (GRAS) ingredient. This combination may be used alone or in combination as a medical food, botanical drug, or pharmaceutical drug to treat angiogenesis-related diseases and conditions such as cancer, obesity, rheumatoid arthritis, retinopathies, and psoriasis.

The present invention provides a method of preventing or ameliorating obesity due to a high fat diet or a disease that causes an angiogenic response in the body such as retinopathy and psoriasis, comprising administering to a subject at risk for a disease or displaying symptoms for such disease, an effective amount of GER. The term "ameliorate" refers to a decrease or lessening of the symptoms or signs of the disorder being treated. The symptoms or signs that may be ameliorated include those associated with an increase in angiogenesis in the body.

The complete disclosures of all references cited in this application are hereby incorporated by reference. The complete disclosure of the following are an integral part of this application: (1) P. Yang et al., "The anti-angiogenic activity of sweet leaf tea extract is mediated by the down-regulation of bFGF and VEGF receptors," an abstract and poster accepted for the American Association for Cancer Research annual meeting, Apr. 18-22, 2009, Denver, Colo.; and (2) G. Chou et al., "Quantitative and fingerprint analyses of Chinese sweet tea plant (*Rubus suavissimus* S. Lee)," J. Agric. and Food Chem., vol. 57, pp. 1076-1083 (2009). In the event of an otherwise irreconcilable conflict, however, the present specification shall control.

What is claimed:

1. A method to decrease symptoms in a mammal on a high fat diet; wherein said decrease in symptoms is selected from the group consisting of decreased weight gain, decreased fat accumulation, decreased serum cholesterol, and decreased serum triglycerides; said method comprising orally administering to the mammal an effective amount of a composition that comprises gallic acid, ellagic acid, and rubusoside in a ratio of about 1:1.7:17; wherein the composition contains no steviol monoside.

2. The method of claim 1, wherein the total mass of gallic acid, ellagic acid, and rubusoside comprises at least 50% of the total mass of the solids of the composition.

3. The method of claim 1, wherein the total mass of gallic acid, ellagic acid, and rubusoside comprises at least 90% of the total mass of the solids of the composition.

4. The method of claim 1, wherein the administration of the composition decreases weight gain.

5. The method of claim 1, wherein the administration of the composition decreases fat accumulation.

6. The method of claim 1, wherein the administration of the composition decreases serum cholesterol.

7. The method of claim 1, wherein the administration of the composition decreases serum triglycerides.

* * * * *